(12) United States Patent
Philip

(10) Patent No.: US 10,155,036 B2
(45) Date of Patent: Dec. 18, 2018

(54) MHC CLASS I ASSOCIATED PEPTIDES FOR PREVENTION AND TREATMENT OF HEPATITIS B VIRUS INFECTION

(71) Applicant: Emergex Vaccines Holding Ltd., Abingdon (GB)

(72) Inventor: Ramila Philip, Ivyland, PA (US)

(73) Assignee: Emergex Vaccines Holding Ltd., Abingdon, Oxford (GB)

( * ) Notice: Subject to any disclaimer, the term of this patent is extended or adjusted under 35 U.S.C. 154(b) by 0 days.

(21) Appl. No.: 15/121,496

(22) PCT Filed: Feb. 13, 2015

(86) PCT No.: PCT/US2015/015807
§ 371 (c)(1),
(2) Date: Aug. 25, 2016

(87) PCT Pub. No.: WO2015/130488
PCT Pub. Date: Sep. 3, 2015

(65) Prior Publication Data
US 2016/0361410 A1    Dec. 15, 2016

Related U.S. Application Data

(60) Provisional application No. 61/946,183, filed on Feb. 28, 2014.

(51) Int. Cl.
| | |
|---|---|
| *A61K 39/29* | (2006.01) |
| *A61K 39/12* | (2006.01) |
| *C07K 14/02* | (2006.01) |
| *C07K 14/005* | (2006.01) |
| *G01N 33/569* | (2006.01) |
| *C12N 7/00* | (2006.01) |
| *A61K 39/00* | (2006.01) |

(52) U.S. Cl.
CPC .............. *A61K 39/29* (2013.01); *A61K 39/12* (2013.01); *C07K 14/005* (2013.01); *C07K 14/02* (2013.01); *C12N 7/00* (2013.01); *G01N 33/56972* (2013.01); *G01N 33/56977* (2013.01); *G01N 33/56994* (2013.01); *A61K 2039/572* (2013.01); *C12N 2730/10121* (2013.01); *C12N 2730/10134* (2013.01); *G01N 2333/02* (2013.01); *G01N 2333/70539* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,690,915 A | 9/1987 | Rosenberg |
| 4,837,028 A | 6/1989 | Allen |
| 4,844,893 A | 7/1989 | Honski |
| 5,017,369 A | 5/1991 | Marhevka |

FOREIGN PATENT DOCUMENTS

WO    WO200100225    *    1/2001

OTHER PUBLICATIONS

Posnett, D. N. et al., J.Biol.Chem., 263:1717-1725, (1788).
Bertoni et al., J Clin Invest., 100(3);503-513, 1997.
Testa et al.,, J Infect Disease, 205;647-655.( 2012).
Betts et al., J Immun Meth., 281:65-78, (2003).
Mittendorf et al, Breast Can Res and Treat, 92:85093 (2005).
Nieminen et al., PLoS ONE: e70738 (2013).
Parmigiani et al., PLoS ONE, 8(11): e79816 (2013).
Bertoletti and Gehring, J Gen Vir, 87:1439-1449 (2006).

* cited by examiner

*Primary Examiner* — Nicole Kinsey White
(74) *Attorney, Agent, or Firm* — Joseph F. Aceto

(57) ABSTRACT

The present invention relates to compositions and methods for the prevention, treatment, and diagnosis of Hepatitis B virus (HBV) infection, and discloses peptides, polypeptides, and polynucleotides that can be used to stimulate a CTL response against HBV infection. The peptide and/or proteins of the invention may be used as a therapeutic drug to stimulate the immune system to recognize and eliminate HBV infection in infected cells or as a vaccine for the prevention of disease.

8 Claims, 3 Drawing Sheets
Specification includes a Sequence Listing.

MHC CLASS I ASSOCIATED PEPTIDES FOR PREVENTION AND TREATMENT OF HEPATITIS B VIRUS INFECTION

CROSS REFERENCE TO RELATED APPLICATIONS

This application is the US national application of PCT/US2015/015807, filed on 13 Feb. 2015 which claims priority to U.S. Provisional application No. 61/946,183, filed on 28 Feb. 2014, the disclosures of which are herein incorporated by reference in its entirety.

FIELD OF THE INVENTION

The present invention relates generally to the field of immunogens whose structures incorporate peptides derived from HBV infection and to methods of using such peptide as a basis for the prevention and treatment of diseases such as HBV infection.

BACKGROUND OF THE INVENTION

The mammalian immune system has evolved a variety of mechanisms to protect the host from microorganisms, an important component of this response being mediated by cells referred to as T cells and by antibodies derived from B cells. In combating bacterial infections, antibodies are especially important but likewise are specialized T cells that function primarily by recognizing and killing infected cells. The latter also function by secreting soluble molecules called cytokines that mediate a variety of functions of the immune system. Thus, the immune system is highly developed to deal with infectious organisms as well as with the elimination of cells infected with such organisms. Among the latter are viral infections, such as HBV infection.

Hepatitis B virus (HBV) is a member of the Hepadnaviridae family of viruses which also includes woodchuck hepatitis virus (WHV) and duck hepatitis B virus. These viruses are primarily hepatotropic with infections characterized by fever, fatigue, muscle aches, and yellowing of the eyes and/or skin. The severity of these symptoms can vary with a proportion of cases being asymptomatic. More than 2.5 billion people worldwide have been infected by HBV, but for the vast majority of adults encountering the virus (>90%), the infection is acute and readily cleared by the immune system. For the remaining 5-10% of adults, and for neonates and unvaccinated children, HBV establishes a chronic infection. Approximately 370 million people worldwide are chronically infected and over 500,000 people die each year due to complications from HBV. These complications include liver cirrhosis, liver failure, and/or hepatocellular carcinoma (HCC) and it is estimated that up to 40% of chronically infected patients will develop at least one of these complications.

The primary determinant of whether hepatitis B virus is cleared or establishes a chronic infection is the robustness of the immune response, in particular the $CD8^+$ T cell response. Data from both animal models and infected patients indicate that strong innate immune responses are crucial in controlling initial HBV replication and for subsequently activating the adaptive T cell response (reviewed in Rehermann and Nascimbeni; Bertoletti and Gehring). In patients that resolve acute infections, there are greater numbers of IFN-γ secreting $CD4^+$ and $CD8^+$ T cells with a broader range of epitope recognition than in chronically infected patients (as reviewed in Bertoletti and Gehring; Desmond et al.).

Although individuals that initially fail to mount vigorous T cell responses develop chronic infection, data indicate that virus specific T cells are still capable of a broad, effective T cell response. Rehermann et al. demonstrated that a small number of chronically infected individuals mount robust CTL responses against HBV either spontaneously or in response to IFN-α treatment. These T cells are directed against multiple proteins indicating that chronically infected patients can also mount a broad response to viral antigens. These data suggest that therapeutic interventions designed to stimulate robust and multi-epitope specific responses may be sufficient to resolve chronic HBV infections. Yet, despite an effective prophylactic vaccine, there are currently no therapies capable of eliminating HBV from chronically infected individuals. A number of anti-HBV therapeutic vaccines have been tested including traditional prophylactic vaccines, antigen/antibody complexes, lipopeptide, DNA, and recombinant virus based strategies with limited success. Thus, there is a critical need for more targeted therapeutic vaccines capable of inducing robust, sustained T cell responses capable of permanent clearance of virus.

Therapeutic peptide based vaccines are an attractive method for inducing $CD4^+$ and $CD8^+$ T cell responses in chronically infected individuals. While other vaccine formulations (such as DNA and recombinant virus vaccines) induce T cell responses, the peptide epitopes generated after vaccination may not accurately reflect those generated during chronic infection and therefore may not induce the necessary polyclonal response needed to clear the virus. In contrast, formulating a vaccine with multiple epitopes presented by the chronically infected cells that are capable of activating T cells to generate a polyclonal response would bypass the need for translation and processing of the parent protein and allow for expansion of the appropriate T cell specificities.

Peptide antigens for these early stage clinical studies were identified by motif prediction algorithms and selected by screening CTLs from acute and chronically HBV infected patients. However, the T cell epitopes presented by HBV infected cells have not been reported or used in a clinical study.

Here we took an immunoproteomic approach to identify MHC class I peptides presented by chronic HBV infected cells. This approach has distinct advantages over traditional vaccine design algorithms as it identifies antigens naturally processed and presented by infected, but not healthy, cells. The identification of peptides and proteins derived from HBV infection that are effectively recognized by the cellular arm of the immune response forms the basis for a new and effective vaccine. Such peptides are displayed on the surface of infected cells in association with MHC class I and class II molecules and serve as recognition targets for cytolytic and helper T cells of the immune system.

The present disclosure involves peptides that are associated with the HLA-A2, and HLA-A24 molecules, HLA-A2 supertypes, and HLA-A24 supertypes. A supertype is a group of HLA molecules that present at least one shared epitope. The present disclosure involves peptides that are associated with HLA molecules, and with the genes and proteins from which these peptides are derived.

Several methods have been developed to identify the peptides recognized by CTL, each method relying on the ability of a CTL to recognize and kill only those cells expressing the appropriate class I MHC molecule with the peptide bound to it. Such peptides can be derived from a non-self source, such as a pathogen (for example, following the infection of a cell by a virus, such as HBV virus infection) or from a self-derived protein within a cell, such as a cancerous cell.

Three different methodologies have typically been used for identifying the peptides that are recognized by CTLs in infectious disease field. These are: (1) the genetic method; (2) motif analysis; (3) the immunological and analytical chemistry methods or the Immunoproteomics method. The genetic and motif prediction methodologies have typically been used for identifying the peptides that are recognized by CTLs, which suffer from various drawbacks. A useful technique has been the immunoproteomics method involving a combination of cellular immunology and mass spectrometry. This approach involves the actual identification of endogenous CTL epitopes present on the cell surface by sequencing the naturally occurring peptides associated with class I MHC molecules. In this approach, cells are first lysed in a detergent solution, the peptides associated with the class I MHC molecules are purified, and the peptides are fractionated by high performance liquid chromatography (HPLC). Peptide sequencing is readily performed by tandem mass spectrometry. The sequence can be confirmed by direct synthesis thereof (See Examples 4 and 5, below). Once confirmed such synthetic peptides can be used to test their ability to activate CTLs against cells infected with the HBV virus.

A number of recent reports for different types of virus infections provide evidence that CTL specific for epitopes that are naturally processed and presented by infected cells have markedly greater impact on the control of virus replication. Undoubtedly, CTLs have been shown to play an important role in the elimination of HBV-infected cells. Thus, identification of antigenic peptides that are presented by infected cells and recognized by epitope-specific CTLs may suggest new ways to suppress viral replication and prevent persistent infection. Multiple peptides from conserved regions of HBV may prove essential in the development of a universally immunogenic vaccine.

Little is known about cross genotypes conserved T cell epitopes that are immunologically relevant in eliciting an effective T cell response to the various HBV genotypes. Several groups have attempted to identify T cell epitopes by either motif prediction of MHC binding peptides from HBV proteins, or by screening overlapping peptides from structural and nonstructural viral proteins. Screening PBMCs from infected individuals using a panel of algorithm-derived peptide sequences identified a few cross genotype specific T cell epitopes. However, a comprehensive analysis of naturally presented epitopes on infected cells has never been undertaken or reported.

Immunization with virus-derived, class I MHC-encoded molecule-associated peptides, or with a precursor polypeptide or protein that contains the peptide, or with a gene that encodes a polypeptide or protein containing the peptide, are forms of immunotherapy that can be employed in the treatment of infections. These forms of immunotherapy require that immunogens be identified so that they can be formulated into an appropriate vaccine.

BRIEF SUMMARY OF THE INVENTION

The present invention relates to Immunogens, such as polypeptides and functionally similar structures, comprising a novel epitopic peptide sequence of between 8 and 14, amino acids in length, most especially the sequence of SEQ ID NO: 1-17 and which immunogens facilitate a cytotoxic T lymphocyte (CTL)-mediated immune response against various strains of HBV infected cells.

The present invention also relates to nucleic acid molecules that encode polypeptides comprising said epitopic peptide, and which can also be used to facilitate an immune response against HBV infected cells.

The present invention provides compositions comprising the polypeptides and immunogens described herein whereby the oligopeptides and polypeptides of such immunogens are capable of inducing a CTL response against cells expressing a protein comprising an epitopic sequence of SEQ ID NO: 1-17 presented in association with Class I MHC protein, which cells are infected with various strains of HBV.

In specific embodiments, the oligopeptides of the invention have a sequence that comprises SEQ ID NO: 1-17 and are used as part of a larger structure, most advantageously a polypeptide, including both naturally occurring polypeptides and synthetic polypeptides. The immunogens of the invention incorporate such epitopic peptide sequences, either with such sequences attached to form a larger antigenic structure or just as part of a polypeptide sequence incorporating such peptides as part of the amino acid sequence thereof in a pharmaceutical composition containing at least one immunogen and a pharmaceutically acceptable carrier.

Where the immunogens of the invention are polypeptides, or mixtures of polypeptides in the form of a pharmaceutically acceptable salt, such polypeptides can be of any length as long as part of their sequence comprises at least one peptide of SEQ ID NO: 1-17, or sequence highly homologous thereto, ordinarily differing by no more than one amino acid residue, including multiple copies of said sequence, when it is desired to induce a CTL response against such peptide and thereby against HBV infected cells.

The present invention further relates to polynucleotides comprising the gene coding for a polypeptide of the immunogens disclosed herein. The present invention also provides methods that comprise contacting a lymphocyte, especially a CTL, with an immunogen or its isoforms or splice variants of the invention under conditions that induce a CTL response against various strains of HBV infected cell, and more specifically HBV A infected cell. The methods may involve contacting the CTL with the immunogenic peptide in vivo, in which case the peptides, polypeptides, and polynucleotides of the invention are used as vaccines, and will be delivered as a pharmaceutical composition comprising a pharmaceutically acceptable carrier or delivery system and the immunogen, typically along with an adjuvant or one or more cytokines.

Alternatively, the immunogens of the present invention can be used to induce a CTL response in vitro. The generated CTL can then be introduced into a patient with HBV infection. Alternatively, the ability to generate CTLs in vitro can serve as a diagnostic for HBV infection.

DETAILED SUMMARY OF THE INVENTION

Figure 1:
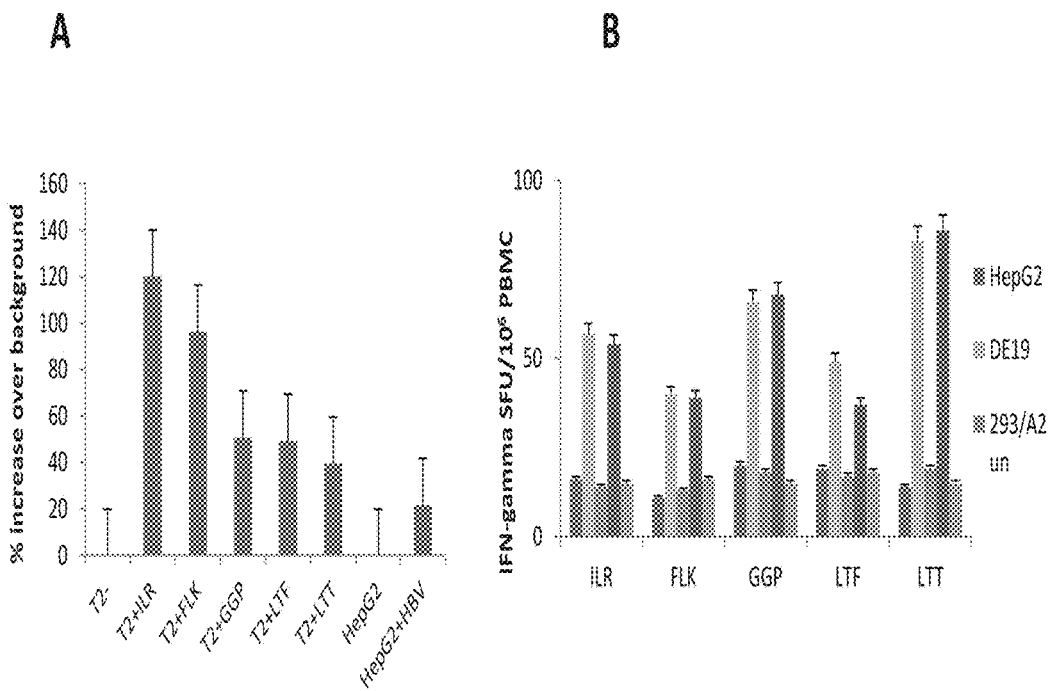
FIG. 1: HBV specific peptides stimulated CD8$^+$ T cell activation in vitro. (A.) HLA-A2 restricted CTLs directed against the identified peptides (peptides are represented as first 3 residues of the sequence) were generated as previously described. PBMCs containing the epitope specific CTLs were harvested, washed, and cultured with the peptide pulsed (A) or HBV expressing cells (B) overnight in an IFN-gamma ELISpot assay. Data is represented as % increase over background. (B.) PBMCs containing epitope specific CTLs were harvested, washed, and cultured with uninfected or HBV expressing cells overnight in an IFN-gamma ELISpot assay. Normal liver cells served as a negative, non-specific control.

As used herein and except as noted otherwise, all terms are defined as given below. The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length. The series of amino acids are consider an "oligopeptide" when the amino acid length is greater than about 14 amino acids in length, typically up to about 30 to 40 residues in length. When the amino acid residue length exceeds 40 amino acid residues, the series of amino acid residues is termed "polypeptide".

A peptide, oligopeptide, polypeptide, protein, or polynucleotide coding for such a molecule is "immunogenic" and thus an immunogen within the present invention if it is capable of inducing an immune response. In the present invention, immunogenicity is more specifically defined as the ability to induce a CTL-mediated response. Thus, an immunogen would be a molecule that is capable of inducing an immune response, and in the present invention, a molecule capable of inducing a CTL response. An immunogen may have one or more isoforms or splice variants that have equivalent biological and immunological activity, and are thus also considered for the purposes of this invention to be immunogenic equivalents of the original, natural polypeptide.

A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length.

Three different genetic loci encode for class I MHC molecules: HLA-A, HLA-B, and HLA-C. The present invention involves peptides that are associated with HLA-A2 supertypes. A supertype is a group of HLA molecules that present at least one shared epitope. MHC molecule peptides that have been found to bind to one member of the MHC allele supertype family (A2 for example) are thought to be likely to bind to other members of the same supertype family (A68 for example).

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The term "nucleotide sequence" refers to a heteropolymer of deoxyribonucleotides. The nucleotide sequence encoding for a particular peptide, oligopeptide, or polypeptide naturally occurring or synthetically constructed.

The term "fragment," when referring to a coding sequence, means a portion of DNA comprising less than the complete coding region whose expression product retains essentially the same biological or immunological function or activity as the expression product of the complete coding region.

The term "isolated" means that the material is removed from its original environment (e.g., the natural environment if it is naturally occurring).

The polynucleotides, and recombinant or immunogenic polypeptides, disclosed in accordance with the present invention may also be in "purified" form.

The term "active fragment" means a fragment that generates an immune response (i.e., has immunogenic activity) when administered, alone or optionally with a suitable adjuvant, to an animal, such as a mammal, for example, a human, such immune response taking the form of stimulating a CTL response within the recipient. Alternatively, the "active fragment" may also be used to induce a CTL response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, the oligopeptides resulting from such treatment would represent portions, segments or fragments of the starting polypeptide.

The term "percent identity" when referring to a sequence, means that a sequence is compared to a described sequence after alignment of the sequence to be compared with the described sequence. The Percent Identity is determined according to the following formula:

Percent Identity=100[1−(C/R)]

wherein C is the number of differences between the Reference Sequence ("R") and the Compared Sequence ("C") over the length of alignment between R and C wherein (i) each base or amino acid in R that does not have a corresponding aligned base or amino acid in the C and (ii) each gap in R and (iii) each aligned base or amino acid in R that is different from an aligned base or amino acid in C, constitutes a difference; and R is the number of bases or amino acids over the length of the alignment with C with any gap created in R also being counted as a base or amino acid.

The present invention relates generally to immunogens and immunogenic compositions, and methods of use thereof, for the prevention, treatment, and diagnosis of HBV viral infections, especially HBV virus infection. Disclosed according to the invention are immunogens comprising proteins or polypeptides whose amino acid sequences comprise one or more epitopic peptides with sequences homologous to, preferably identical to, the sequence of SEQ ID NO:

1-17. In addition, the invention further relates to polynucleotides that can be used to stimulate a CTL response against HBV-infected cells, especially cells infected with the causative organism of HBV virus.

In accordance with the present invention there are disclosed specific amino acid sequences (SEQ ID NO: 1-17) which represent epitopic peptides (i.e. immunogenic peptide sequences) of at least about 8 amino acids in length and no longer than about 14 amino acids in length and which are present as part of a larger structure, such as a polypeptide or full length protein, to form an immunogen of the invention. Proteins present in the cells of HBV infection show these sequences. In addition, synthetic oligopeptides and polypeptides according to the invention also contain this sequence in one or more copies.

When the immunogens of the present invention comprise, or are formed of, polypeptides, these have amino acid sequences that comprise at least one stretch, possibly two, three, four, or more stretches of about 8 to 14 residues in length and wherein any such segment within such sequence differs in amino acid sequence from the sequence of SEQ ID NO: 1-17 by no more than about 1 amino acid residue, giving an overall sequence identity or homology of at least about 88%, preferably a conservative amino acid residue, especially amino acids of the same general chemical character, such as where they are hydrophobic amino acids, or polar amino acids, or acidic amino acids or basic (alkaline) amino acids.

The present invention is also directed to an isolated polypeptide, especially one having immunogenic activity, the sequence of which comprises within it one or more stretches comprising any 2 or more of the sequences of SEQ ID NO: 1-17 and in any relative quantities and wherein said sequences may differ by one amino acid residues from the sequences of SEQ ID NO: 1-17 in any given stretch of 8 to 10, or up to 14 amino acid residues. Thus, within the present invention, by way of a non-limiting example only, such polypeptide may contain as part of its amino acid sequence, nanopeptide fragments having up to 8 amino acids identical to a sequence of SEQ ID NO: 1, 2, 7, 8 such that the polypeptide comprises, in a specific embodiment, 2 segments with at least 8 residues identical to SEQ ID NO: 1 and SEQ ID NO: 2 and one segment with at least 8 residues identical to SEQ ID NO: 7. In other embodiments, other combinations and permutations of the epitopic sequences disclosed herein may be part of an immunogen of the present invention or of such a polypeptide so long as any such polypeptide comprises at least 2 such epitopes, whether such epitopes are different or the same. Thus, in a specific embodiment, a polypeptide of the present invention may comprise 2 copies of the sequence of SEQ ID NO: 2 at some point or points within its length. Of course, any combinations and permutations of the epitopes disclosed herein, as long as they are present at least two in number in such polypeptides, are expressly contemplated.

Peptides of the invention are commonly immunogens, or at least can have immunogenic activity, possibly requiring a larger carrier molecule to facilitate such activity, or said peptides may have immunogenic activity when part of a larger structure, such as a polypeptide, other than the protein found in the HBV organism itself. Such peptides may also have immunogenic activity when part of a composition containing one or more of said epitopic peptides, which may be present in any combination and with each such peptide being present in one or more copies.

Said polypeptides can be of any desired length so long as they have immunogenic activity in that they are able, under a given set of desirable conditions, to elicit in vitro or in vivo the activation of cytotoxic T lymphocytes (CTLs) (i.e., a CTL response) against a presentation of a HBV-infected cell, and when such proteins are presented along with MHC-1 proteins, such as where said proteins are presented in vitro or in vivo by an antigen presenting cell (APC). The proteins and polypeptides forming the immunogens of the present invention can be naturally occurring or may be synthesized chemically.

The epitopic sequence (SEQ ID NO: 1-17) present within polypeptides and proteins forming the immunogens of the present invention include sequences as short as 7, preferably 8, amino acid residues and as long as 15, preferably 14, amino acids in length. The present invention also encompasses peptides at least about 88% identical to the peptides or sequences of SEQ ID NO: 1-17 disclosed herein and to sequences differing from these sequences by no more than one amino acid, including fragments containing sequences having at least 8 residues in common with the sequences of SEQ ID NO: 1-17 over any nine residue length and wherein said homologous sequence of residues need not be continuous so that said length may contain up to one amino acid not in common with the sequence of SEQ ID NO: 1-17 or be identical to said sequence but include one additional residue or have one less residue relative to said sequence and whereby such different amino acid unit or residue may occur anywhere within the corresponding stretch within said immunogen or polypeptide.

The present invention is also directed to an isolated polypeptide, including a purified polypeptide, especially one having immunogenic activity, the sequence of which comprises within it one or more copies of epitopic peptide sequences homologous, if not identical, to the sequence of SEQ ID NO: 1-17 and wherein said sequences may differ by one amino acid residues from the sequence of SEQ ID NO: 1-17. Thus, within the present invention, such polypeptide may contain as part of its amino acid sequence, oligopeptides having up to 8 amino acids in length and differing by no more than one amino acid residue as compared to the sequence of SEQ ID NO: 1-17 such that the polypeptide comprises, in one specific embodiment, 2 segments each with a sequence differing by no more than one amino acid residue from SEQ ID NO: 1-17 and 1 segment identical to SEQ ID NO: 1-17. In other embodiments, other combinations and permutations of the epitopic sequence disclosed herein may be part of an immunogen of the present invention or of such a polypeptide so long as any such polypeptide comprises at least 2 such epitopes, whether such epitopes are identical or differ by a residue. In other preferred embodiments, such immunogen, especially where a polypeptide, may comprise as part of its amino acid sequence, a number of oligopeptide segments as disclosed herein such that there are 2, 3, 4, 5, or more such segments and wherein such segments are contiguous or are not contiguous or where some are contiguous and some are not contiguous.

The present invention further relates to isolated oligopeptides of at least 8 but not more than 14 amino acid units in length and having a sequence differing at most by no more than one amino acid residue from a sequence selected from the group consisting of the sequence of SEQ ID NO: 1-17. Thus, the present invention relates to a immunogen comprising a peptide segment of at least 8 but not more than 14 amino acid units in length which segment comprises a sequence selected from the group consisting of the sequence of SEQ ID NO: 1-17 or a sequence differing from said sequence by not more than 1 amino acid.

In preferred embodiments, where the isolated oligopeptides of the invention are homologous to the sequences of SEQ ID NO: 1-17, said difference of one amino acid residue is the result of a substitution of one hydrophobic amino acid unit by another hydrophobic amino acid, or is the result of a substitution of one polar amino acid unit by another polar amino acid, or is a substitution of one acidic amino acid unit by another acidic amino acid, or is the result of a substitution of one basic amino acid unit by another basic amino acid.

The present invention further relates to a composition comprising one or more of the isolated oligopeptides of the invention suspended in a pharmacologically acceptable carrier or vaccine delivery vehicle.

Oligopeptides as disclosed herein may themselves be prepared by methods well known to those skilled in the art. (Grant, G. A., Synthetic Peptides: A User's Guide, 1792, W. H. Freeman and Company, New York; Coligan, J. E. et al, Current Protocols in Protein Science, 1799, John Wiley & Sons, Inc., New York).

Besides the sequences of SEQ ID NO: 1-17, the proteins and polypeptides forming the immunogens of the present invention may also comprise one or more other immunogenic amino acid stretches known to be associated with various strains of HBV infection, and which may stimulate or enhance a CTL response whereby the immunogenic peptides associate with HLA-A2 or A24 supertypes or another class I MHC (i.e., MHC-1) molecule.

The immunogens of the present invention can be in the form of a composition of one or more of the different immunogens and wherein each immunogen is present in any desired relative abundance. Such compositions can be homogeneous or heterogeneous with respect to the individual immunogens or polypeptides of the invention, or the immunogenic peptide components present in such polypeptides or proteins or immunogens, having only one or more than one of such peptides. For example, an isolated peptide of the present invention can have the sequence of SEQ ID NO: 1-17 or differ there from by 1 amino acid and such peptides can be used to form an immunogenic composition of said peptides as already disclosed herein.

The oligopeptides and polypeptides useful in practicing the present invention may be derived by fractionation of naturally occurring proteins by methods such as protease treatment, or they may be produced by recombinant or synthetic methodologies that are well known and clear to the skilled artisan (Ausubel, F. M. et al, Current Protocols in Molecular Biology, 1799, John Wiley & Sons, Inc., New York; Coligan, J. E. et al, Current Protocols in Protein Science, 1799, John Wiley & Sons, Inc., New York; Molecular Cloning: A Laboratory Manual, 1789, Cold Spring Harbor Laboratory Press, Cold Spring Harbor). The polypeptide may comprise a recombinant or synthetic polypeptide that comprises at least one of SEQ ID NO: 1-17 which sequences may also be present in multiple copies. Thus, oligopeptides and polypeptides of the present invention may have one, two, three, or more such immunogenic peptides within the amino acid sequence of said oligopeptides and polypeptides, and said immunogenic peptides, or epitopes, may be the same or may be different, or may have any number of such sequences wherein some of them are identical to each other in amino acid sequence while others within the same polypeptide sequence are different from each other and said epitopic sequences may occur in any order within said immunogenic polypeptide sequence. The location of such sequences within the sequence of a polypeptide forming an immunogen of the invention may affect relative immunogenic activity. In addition, immunogens of the present invention may comprise more than one protein comprising the amino acid sequences disclosed herein. Such polypeptides may be part of a single composition or may themselves be covalently or non-covalently linked to each other.

Where the immunogen comprises two or more immunogenic epitopes, or epitopic peptides, they may be linked directly together, or through a spacer or linker, to form a larger structure, such as an oligopeptide, or polypeptide, or some other polymeric structure. The epitopic peptides may therefore be linked by any and all means that can be devised by the chemist so long as the immunogenic activity of the overall structure or complex is maintained or, at least, not reduced below a level useful for the methods of the invention (i.e., especially where said immunogenic activity comprises being capable of eliciting a CTL response).

Likewise, the immunogenic peptides disclosed herein may also be linked directly to, or through, a spacer or linker to: an immunogenic carrier such as serum albumin, tetanus toxoid, keyhole limpet hemocyanin, dextran, or a recombinant virus particle or any synthetic nanoparticles such as liposimes, polymers and metal such as gold nanoparticles; an immunogenic peptide known to stimulate a T helper cell type immune response; a cytokine such as interferon gamma or GMCSF (Granulocyte-Monocyte Colony Stimulating Factor); a targeting agent such as an antibody or receptor ligand; a stabilizing agent such as a lipid; or a conjugate of a plurality of epitopes to a branched lysine core structure, such as the so-called "multiple antigenic peptide" described in (Posnett, D. N. et al., J. Biol. Chem., 263:1717-1725, (1788)); a compound such as polyethylene glycol to increase the half life of the peptide; or additional amino acids such as a leader or secretory sequence, or a sequence employed for the purification of the mature sequence.

Useful spacers and linkers are typically comprised of relatively small, neutral molecules, such as amino acids and which are substantially uncharged under physiological conditions. Such spacers are typically selected from the group of nonpolar or neutral polar amino acids, such as glycine, alanine, serine and other similar amino acids. Such optional spacers or linkers need not be comprised of the same residues and thus may be either homo- or hetero-oligomers. When present, such linkers will commonly be of length at least one or two, commonly 3, 4, 5, 6, and possibly as much as 10 or even up to 20 residues (in the case of amino acids). In addition, such linkers need not be composed of amino acids but any oligomeric structures will do as well so long as they provide the correct spacing so as to optimize the desired level of immunogenic activity of the immunogens of the present invention. The immunogen may therefore take any form that is capable of eliciting a CTL response.

In addition, the immunogenic peptides of the present invention may be part of an immunogenic structure via attachments other than conventional peptide bonds. Thus, any manner of attaching the peptides of the invention to an immunogen of the invention, such as an immunogenic polypeptide as disclosed herein, could provide an immunogenic structure as claimed herein. Thus, immunogens, such as proteins of the invention, are structures that contain the peptides disclosed according to the present invention but such immunogenic peptides may not necessarily be attached thereto by the conventional means of using ordinary peptide bounds. The immunogens of the present invention simply contain such peptides as part of their makeup, but how such peptides are to be combined to form the final immunogen is left to the talent and imagination of the user and is in no way restricted or limited by the disclosure contained herein.

The peptides that are naturally processed and bound to a class I MHC molecule in accordance with the invention need not be the optimal peptides for stimulating a CTL response. See, for example, (Parkhurst, M. R. et al., J. Immunol., 157:2539-2548, (1796); Rosenberg, S. A. et al., Nat. Med., 4:321-327, (1798)). Thus, there can be utility in modifying a peptide, such that it more readily induces a CTL response. Generally, peptides may be modified at two types of positions. The peptides may be modified at amino acid residues that are predicted to interact with the class I MHC molecule, in which case the goal is to create a peptide that has a higher affinity for the class I MHC molecule than does the parent peptide. The peptides can also be modified at amino acid residues that are predicted to interact with the T cell receptor on the CTL, in which case the goal is to create a peptide that has a higher affinity for the T cell receptor than does the parent peptide. Both of these types of modifications can result in a variant peptide that is related to a parent peptide, but which is better able to induce a CTL response than is the parent peptide. As used herein, the term "parent peptide" means an oligopeptide having the sequence of SEQ ID NO: 1-17.

The parent peptides disclosed herein can be modified by the substitution of one or more residues at different, possibly selective, sites within the peptide chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, lie, Val, Cys); and Group 4—large, aromatic residues (Phe, Tyr, Trp). An acidic amino acid might also be substituted by a different acidic amino acid or a basic (i.e., alkaline) amino acid by a different basic amino acid.

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such radical substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or syngeneic effects on the antigenicity of the peptide. At most, no more than 1 position (possibly 2 positions) within the peptide would simultaneously be substituted.

Based on cytotoxicity assays, an epitope is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector:target ratio at which the comparison is being made.

Preferably, when the CTLs specific for an oligopeptide of the invention is tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

It should be appreciated that an immunogen may consist only of a peptide of SEQ ID NO: 1-17, or comprise a peptide of SEQ ID NO: 1-17, or comprise a plurality of peptides selected from SEQ ID NO: 1-17, or comprise a polypeptide that itself comprises one or more of the epitopic peptides of SEQ ID NO: 1-17.

The immunogenic peptides and polypeptides of the invention can be prepared synthetically, by recombinant DNA technology, or they can be isolated from natural sources such as tumor cells expressing the original protein product.

The polypeptides and oligopeptides disclosed herein can be synthesized in solution or on a solid support in accordance with conventional techniques. Various automated peptide synthesizers are commercially available and can be used in accordance with known protocols. See, for example, (Grant, G. A., Synthetic Peptides: A User's Guide, 1792, W. H. Freeman and Company, New York; Coligan, J. E. et al, Current Protocols in Protein Science, 1799, John Wiley & Sons, Inc., New York). Fragments of polypeptides of the invention can also be synthesized as intermediates in the synthesis of a larger polypeptide.

Recombinant DNA technology may be employed wherein a nucleotide sequence which encodes an immunogenic peptide or polypeptide of interest is inserted into an expression vector, transformed or transfected into an appropriate host cell, and cultivated under conditions suitable for expression. These procedures are well known in the art to the skilled artisan, as described in (Coligan, J. E. et al, Current Protocols in Immunology, 1799, John Wiley & Sons, Inc., New York; Ausubel, F. M. et al, Current Protocols in Molecular Biology, 1799, John Wiley & Sons, Inc., New York; Molecular Cloning: A Laboratory Manual, 1789, Cold Spring Harbor Laboratory Press, Cold Spring Harbor). Thus, recombinantly produced peptides or polypeptides can be used as the immunogens of the invention.

The coding sequences for peptides of the length contemplated herein can be synthesized on commercially available automated DNA synthesizers using protocols that are well known in the art. See for example, (Grant, G. A., Synthetic Peptides: A User's Guide, 1792, W. H. Freeman and Company, New York; Coligan, J. E. et al, Current Protocols in Protein Science, 1799, John Wiley & Sons, Inc., New York). The coding sequences can also be modified such that a peptide or polypeptide will be produced that incorporates a desired amino acid substitution. The coding sequence can be provided with appropriate linkers, be ligated into suitable expression vectors that are commonly available in the art, and the resulting DNA or RNA molecule can be transformed or transfected into suitable hosts to produce the desired fusion protein. A number of such vectors and suitable host systems are available, and their selection is left to the skilled artisan. For expression of the fusion proteins, the coding sequence will be provided with operably linked start and stop codons, promoter and terminator regions, and a replication system to provide an expression vector for expression in the desired host cell. For example, promoter sequences compatible with bacterial hosts are provided in plasmids containing convenient restriction sites for insertion of the desired coding sequence. The resulting expression vectors are transformed into suitable bacterial hosts. Of course, yeast, insect, and mammalian host cells may also be used, employing suitable vectors and control sequences.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Ausubel, F. M. et al, Current Protocols in Molecular Biology, 1799, John Wiley & Sons, Inc., New York; Molecular Cloning: A Laboratory Manual, 1789, Cold Spring Harbor Laboratory Press, Cold Spring Harbor). Such cells can routinely be utilized for assaying CTL activity by having said genetically engineered, or recombinant, host cells express the immunogenic peptides of the present invention.

Various mammalian cell culture systems can also be employed to express recombinant protein. Examples of mammalian expression systems include the COS-7 lines of monkey kidney fibroblasts, described by Gluzman, Cell, 23:175 (1781), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The immunogenic peptides of the present invention may be used to elicit CTLs ex vivo from either healthy individuals or from patients with HBV infection (or at risk thereof). Such responses are induced by incubating in tissue culture the individual's CTL precursor lymphocytes together with a source of antigen presenting cells and the appropriate immunogenic peptide. Examples of suitable antigen presenting cells include dendritic cells, macrophages, and activated B cells. Typically, the peptide at concentrations between 10 and 40.mu.g/ml, would be pre-incubated with the antigen presenting cells for periods ranging from 1 to 18 hrs. .beta. .sub.2-microglobulin (4.mu.g/ml) can be added during this time period to enhance binding. The antigen presenting cells may also be held at room temperature during the incubation period (Ljunggren, H.-G. et al., Nature, 346:476-480, (1790)) or pretreated with acid (Zeh, H. J., III et al., Hum. Immunol., 39:79-86, (1794)) to promote the generation of denatured class I MHC molecules which can then bind the peptide. The precursor CTLs (responders) are then added to the antigen presenting cells to which the immunogenic peptide has bound (stimulators) at responder to stimulator ratios of between 5:1 and 50:1, and most typically between 10:1 and 20:1. The co-cultivation of the cells is carried out at 37.degree. C. in RPMI 1640, 10% fetal bovine serum, 2 mM L-glutamine, and IL-2 (5-20 Units/ml). Other cytokines, such as IL-1, IL-7, and IL-12 may also be added to the culture. Fresh IL-2-containing media is added to the cultures every 2-4 days, typically by removing one-half the old media and replenishing it with an equal volume of fresh media. After 7-10 days, and every 7-10 days thereafter, the CTL are restimulated with antigen presenting cells to which immunogenic peptide has been bound as described above. Fresh IL-2-containing media is added to the cells throughout their culture as described above. Three to four rounds of stimulation, and sometimes as many five to eight rounds of stimulation, are required to generate a CTL response that can then be measured in vitro. The above described protocol is illustrative only and should not be considered limiting. Many in vitro CTL stimulation protocols have been described and the choice of which one to use is well within the knowledge of the skilled artisan. The peptide-specific CTL can be further expanded to large numbers by treatment with anti-CD3 antibody. For example, see (Riddell, S. R. and Greenberg, P. D., J. Immunol. Methods, 128:189-201, (1790); Walter, E. A. et al., N. Engl. J. Med., 333:1038-1044, (1795)).

Antigen presenting cells that are to be used to stimulate a CTL response are typically incubated with peptide of an optimal length as disclosed herein that allows for direct binding of the peptide to the class I MHC molecule without additional processing. Larger oligopeptides and polypeptides are generally ineffective in binding to class I MHC molecules as they are not efficiently processed into an appropriately sized peptide in the extracellular milieu. There are a variety of approaches that are known in the art, however, that allow oligopeptides and polypeptides to be exogenously acquired by a cell, which then allows for their subsequent processing and presentation by a class I MHC molecule. Representative, but non-limiting examples of such approaches include electroporation of the molecules into the cell (Harding, C. H. III, Eur. J. Immunol., 22:1865-1869, (1792)), encapsulation of the molecules in liposomes which are fused to the cells of interest (Reddy, R. et al., J. Immunol. Methods, 141:157-163, (1791)), or osmotic shock in which the molecules are taken up via pinocytosis (Moore, M. W. et al., Cell, 54:777-717, (1788)). Thus, oligopeptides and polypeptides that comprise one or more of the peptides of the invention can be provided to antigen presenting cells in such a fashion that they are delivered to the cytoplasm of the cell, and are subsequently processed to allow presentation of the peptides.

Antigen presenting cells suitable for stimulating an in vitro CTL response that is specific for one or more of the peptides of the invention can also be prepared by introducing polynucleotide vectors encoding the sequences into the cells. These polynucleotides can be designed such that they express only a single peptide of the invention, multiple peptides of the invention, or even a plurality of peptides of the invention. There are a variety of approaches that are known in the art, that allow polynucleotides to be introduced and expressed in a cell, thus providing one or more peptides of the invention to the class I MHC molecule binding pathway. Representative, but non-limiting examples of such approaches include the introduction of plasmid DNA through particle-mediated gene transfer or electroporation (Tuting, T. et al., J. Immunol., 160:1139-1147, (1798)), or the transduction of cells with an adenovirus expressing the polynucleotide of interest (Perez-Diez, A. et al., Cancer Res., 58:5305-5309, (1798)). Thus, oligonucleotides that code for one or more of the peptides of the invention can be provided to antigen presenting cells in such a fashion that the peptides associate with class I MHC molecules and are presented on the surface of the antigen presenting cell, and consequently are available to stimulate a CTL response.

By preparing the stimulator cells used to generate an in vitro CTL response in different ways, it is possible to control the peptide specificity of CTL response. For example, the CTLs generated with a particular peptide will necessarily be specific for that peptide. Likewise, CTLs that are generated with a polypeptide or polynucleotide expressing or coding for particular peptides will be limited to specificities that recognize those peptides. More broadly, stimulator cells, and more specifically dendritic cells, can be incubated in the presence of the whole parent protein. As a further alternative, stimulator cells, and more specifically dendritic cells, can be transduced or transfected with RNA or DNA comprising the polynucleotide sequence encoding the protein. Under these alternative conditions, peptide epitopes that are naturally cleaved out of the protein, and which are generated in addition to peptide epitopes of SEQ ID NO: 1-17 can associate with an appropriate class I MHC molecule, which may or may not include HLA-A1, -A2, -A24. The selection of antigen presenting cells and the type of antigen with which to stimulate the CTL, is left to the ordinary skilled artisan.

In certain embodiments, the methods of the present invention include a method for inducing a CTL response in vitro that is specific for a tumor cell expressing a molecule from A1, A2, or A24 supertypes, whereby the method comprises contacting a CTL precursor lymphocyte with an antigen presenting cell that has bound an immunogen comprising one or more of the peptides disclosed according to the invention.

In specific embodiments, the methods of the present invention include a method for inducing a CTL response in vitro that is specific for a tumor cell expressing a molecule from A1, A2, or A24 supertypes, whereby the method comprises contacting a CTL precursor lymphocyte with an antigen presenting cell that has exogenously acquired an immunogenic oligopeptide or polypeptide that comprises one or more of the peptides disclosed according to the invention.

A yet additional embodiment of the present invention is directed to a process for inducing a CTL response in vitro that is specific for a tumor cell expressing a molecule from A1, A2, or A24 supertypes, comprising contacting a CTL precursor lymphocyte with an antigen presenting cell that is expressing a polynucleotide coding for a polypeptide of the invention and wherein said polynucleotide is operably linked to a promoter.

A variety of techniques exist for assaying the activity of CTL. These techniques include the labeling of target cells with radionuclides such as $Na_2^{51}CrO_4$ or $^3H$-thymidine, and measuring the release or retention of the radionuclides from the target cells as an index of cell death. Such assays are well-known in the art and their selection is left to the skilled artisan. Alternatively, CTLs are known to release a variety of cytokines when they are stimulated by an appropriate target cell, such as a cell expressing the relevant class I MHC molecule and the corresponding peptide. Non-limiting examples of such cytokines include IFN-$\gamma$, TNF-$\alpha$, and GM-CSF. Assays for these cytokines are well known in the art, and their selection is left to the skilled artisan. Methodology for measuring both target cell death and cytokine release as a measure of CTL reactivity are given in (Coligan, J. E. et al, Current Protocols in Immunology, 1799, John Wiley & Sons, Inc., New York).

After expansion of the antigen-specific CTLs, the latter are then adoptively transferred back into the patient, where they will destroy their specific target cell, especially macrophages infected with M. HBV infection. The utility of such adoptive transfer is demonstrated in (North, R. J. et al., Infect. Immun., 67:2010-2012, (1799); Riddell, S. R. et al., Science, 257:238-241, (1792)). In determining the amount of cells to re-infuse, the skilled physician will be guided by the total number of cells available, the activity of the CTL as measured in vitro, and the condition of the patient. Preferably, however, about $1 \times 10^6$ to about $1 \times 10^{12}$, more preferably about $1 \times 10^8$ to about 1.times.10.sup.11, and even more preferably, about 1.times.10.sup.9 to about 1.times.10.sup.10 peptide-specific CTL are infused. Methodology for re-infusing the T cells into a patient are well known and exemplified in U.S. Pat. No. 4,844,893 to Honski, et al., and U.S. Pat. No. 4,690,915 to Rosenberg.

The peptide-specific CTL can be purified from the stimulator cells prior to infusion into the patient. For example, monoclonal antibodies directed towards the cell surface protein CD8, present on CTL, can be used in conjunction with a variety of isolation techniques such as antibody panning, flow cytometric sorting, and magnetic bead separation to purify the peptide-specific CTL away from any remaining non-peptide specific lymphocytes or from the stimulator cells. These methods are well known in the art, and are their selection is left to the skilled artisan. It should be appreciated that generation of peptide-specific CTL in this manner, obviates the need for stimulating the CTL in the presence of tubercle-infected cells. Thus, there is no chance of inadvertently reintroducing infected cells into the patient.

Thus, one embodiment of the present invention relates to a process for treating a subject with cancer characterized by tumor cells expressing complexes of a molecule from A1, A2, or A24 supertypes, for example, HLA-A1, HLA-A2, or HLA-A24, whereby CTLs produced in vitro according to the present invention are administered in an amount sufficient to destroy the tumor cells through direct lysis or to effect the destruction of the tumor cells indirectly through the elaboration of cytokines.

Another embodiment of the present invention is directed to a process for treating a subject with cancer characterized by tumor cells expressing any class I MHC molecule and an epitope of SEQ ID NO: 1-17, whereby the CTLs are produced in vitro and are specific for the epitope or original protein and are administered in an amount sufficient to destroy the tumor cells through direct lysis or to effect the destruction of the tumor cells indirectly through the elaboration of cytokines.

In additional embodiments, ex vivo generated CTLs can be used to identify and isolate the T cell receptor molecules specific for the peptide. The genes encoding the alpha and beta chains of the T cell receptor can be cloned into an expression vector system and transferred and expressed in nave T cells from peripheral blood, T cells from lymph nodes, or T lymphocyte progenitor cells from bone marrow. These T cells, which would then be expressing a peptide-specific T cell receptor, would then have specific cytotoxic reactivity and could be used in adoptive therapy to destroy HBV infected cells.

In addition to their use for therapeutic or prophylactic purposes, the immunogenic peptides of the present invention are useful as screening and diagnostic agents. Thus, the immunogenic peptides of the present invention, together with modern techniques of gene screening, make it possible to screen patients for the presence of genes encoding such peptides on cells obtained from patients suspected of infection and possibly the results of such screening may help determine the efficacy of HBV vaccines for protection against various strains of HBV infection. Proceeding with the regimen of treatment disclosed herein using the immunogens of the present invention.

Alternatively, the immunogenic peptides disclosed herein, as well as functionally similar homologs thereof, may be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, and pleural fluid. The peptides of the present invention may then be used as a diagnostic tool to evaluate the efficacy of the immunotherapeutic treatments disclosed herein. Thus, the in vitro generation of CTLs as described above would be used to determine if patients are likely to respond to the peptide in vivo. Similarly, the in vitro generation of CTLs could be done with samples of lymphocytes obtained from the patient before and after treatment with the peptides and other immunogens of the invention. Successful generation of CTLs in vivo should then be recognized by a correspondingly easier ability to generate peptide-specific CTLs in vitro from lymphocytes obtained following treatment in comparison to those obtained before treatment.

The oligopeptides of the invention, such as SEQ ID NO: 1-17, can also be used to prepare class I MHC tetramers which can be used in conjunction with flow cytometry to quantitate the frequency of peptide-specific CTL that are present in a sample of lymphocytes from an individual. Specifically, for example, class I MHC molecules comprising HLA-A2 and peptides highly homologous, meaning differing by 1 amino acid residue, including where, for example, the peptide sequence has 8 or 10 residues, to SEQ ID NO:1 would be combined to form tetramers as exemplified in U.S. Pat. No. 5,635,363. Said tetramers would find use in monitoring the frequency of CTLs in the peripheral blood, lymph nodes, or tumor mass of an individual undergoing immunotherapy with the peptides, proteins, or polynucleotides of the invention, and it would be expected that successful immunization would lead to an increase in the frequency of the peptide-specific CTL.

As stated above, a vaccine in accordance with the present invention may include one or more of the hereinabove described polypeptides or active fragments thereof, or a composition, or pool, of immunogenic peptides disclosed herein. When employing more than one polypeptide or active fragment, such as two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

The immunogenic molecules of the invention, including vaccine compositions, may be utilized according to the present invention for purposes of preventing, suppressing or treating diseases causing the expression of the immunogenic peptides disclosed herein, such as where the antigen is being expressed by HBV infected cells. As used in accordance with the present invention, the term "prevention" relates to a process of prophylaxis in which an animal, especially a mammal, and most especially a human, is exposed to an immunogen of the present invention prior to the induction or onset of the disease process. Thus, the immunogen could be administered to the general population as is frequently done for infectious diseases. Alternatively, the term "suppression" is often used to describe a condition wherein the disease process has already begun but obvious symptoms of said condition have yet to be realized. Thus, the cells of an individual may have become infected but no outside signs of the disease have yet been clinically recognized. In either case, the term prophylaxis can be applied to encompass both prevention and suppression. Conversely, the term "treatment" is often utilized to mean the clinical application of agents to combat an already existing condition whose clinical presentation has already been realized in a patient. This would occur where an individual has already been diagnosed as having an HBV infection.

It is understood that the suitable dosage of an immunogen of the present invention will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician. The total dose required for any given treatment will commonly be determined with respect to a standard reference dose as set by a manufacturer, such as is commonly done with vaccines, such dose being administered either in a single treatment or in a series of doses, the success of which will depend on the production of a desired immunological result (i.e., successful production of a CTL-mediated response to the antigen, which response gives rise to the prevention and/or treatment desired). Thus, the overall administration schedule must be considered in determining the success of a course of treatment and not whether a single dose, given in isolation, would or would not produce the desired immunologically therapeutic result or effect.

The therapeutically effective amount of a composition containing one or more of the immunogens of this invention is an amount sufficient to induce an effective CTL response to the antigen and to cure or arrest disease progression. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Thus, for purposes of prophylactic or therapeutic administration, effective amounts would generally lie within the range of from 1.0 µg to about 5,000 µg of peptide for a 70 kg patient, followed by boosting dosages of from about 1.0 µg to about 1,000 µg of peptide pursuant to a boosting regimen over days, weeks or even months, depending on the recipient's response and as necessitated by subsequent monitoring of CTL-mediated activity within the bloodstream. Of course, such dosages are to be considered only a general guide and, in a given situation, may greatly exceed such suggested dosage regimens where the clinician believes that the recipient's condition warrants more aggressive administration schedule. Needless to say, the efficacy of administering additional doses, and of increasing or decreasing the interval, may be re-evaluated on a continuing basis, in view of the recipient's immunocompetence.

For such purposes, the immunogenic compositions according to the present invention may be used against a disease condition such as HBV infection by administration to an individual by a variety of routes. The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used. These compositions may be sterilized by conventional, well known sterilization techniques including sterile filtration. The resulting solutions may be packaged for use as is, or the aqueous solutions may be lyophilized, the lyophilized preparation being combined with sterile water before administration. Vaccine compositions may further incorporate additional substances to stabilize pH, or to function as adjuvants, wetting agents, or emulsifying agents, which can serve to improve the effectiveness of the vaccine.

The concentration of the CTL stimulatory peptides of the invention in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, possibly PBS (phosphate buffered saline), or saline itself, or other possible carriers or excipients.

The immunogens of the present invention may also be contained in artificially created structures such as liposomes, ISCOMS, slow-releasing nanoparticles, and other vehicles which increase the immunogenicity and/or half-life of the peptides or polypeptides in serum. Liposomes include emulsions, foams, micelles, insoluble monolayers, liquid crystals, phospholipid dispersions, lamellar layers and the like. Liposomes for use in the invention are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by (Coligan, J. E. et al, Current Protocols in Protein Science, 1799, John Wiley & Sons, Inc., New York) and see also U.S. Pat. Nos. 4,235,871, 4,501,728, 4,837,028, and 5,017,369.

Liposomes containing the peptides or polypeptides of the invention can be directed to the site of lymphoid cells where the liposomes then deliver the selected immunogens directly to antigen presenting cells. Targeting can be achieved by incorporating additional molecules such as proteins or polysaccharides into the outer membranes of said structures, thus resulting in the delivery of the structures to particular areas of the body, or to particular cells within a given organ or tissue. Such targeting molecules may be a molecule that binds to receptor on antigen presenting cells. For example an antibody that binds to CD80 could be used to direct liposomes to dendritic cells.

The immunogens of the present invention may also be administered as solid compositions. Conventional nontoxic solid carriers including pharmaceutical grades of mannitol, lactose, starch, magnesium, cellulose, glucose, sucrose, sodium saccharin, and the like. Such solid compositions will often be administered orally, whereby a pharmaceutically acceptable nontoxic composition is formed by incorporating the peptides and polypeptides of the invention with any of the carriers listed above. Generally, such compositions will contain 10-95% active ingredient, and more preferably 25-75% active ingredient.

Aerosol administration is also an alternative, requiring only that the immunogens be properly dispersed within the aerosol propellant. Typical percentages of the peptides or polypeptides of the invention are 0.01%-20% by weight, preferably 1%-10%. The use of a surfactant to properly disperse the immunogen may be required. Representative surfactants include the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. Typical propellants for such administration may include esters and similar chemicals but are by no means limited to these. A carrier, such as lecithin for intranasal delivery, may also be included.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, basic salts of acid moieties which may be present on a peptide are prepared using a pharmaceutically acceptable base such as sodium hydroxide, potassium hydroxide, ammonium hydroxide, calcium hydroxide, trimethylamine or the like.

A preferred embodiment of the pharmaceutical compositions comprise the peptides as salts of acetic acid (acetates), ammonium or hydrochloric acid (chlorides).

In another embodiment, a pharmaceutical composition of the present invention may include sugars, sugar alcohols, amino acids such as glycine, arginine, glutaminic acid and others as framework former. The sugars may be mono-, di- or trisaccharide. These sugars may be used alone, as well as in combination with sugar alcohols. Examples of sugars include glucose, mannose, galactose, fructose or sorbose as monosaccharides, saccharose, lactose, maltose or trechalose as disaccharides and raffinose as a trisaccharide. A sugar alcohol may be, for example, manniose, Preferred ingredients are saccharose, lactose, maltose, trehalose, mannitol and/or sorbitol, and more preferably, mannitol.

Pharmaceutical compositions of the present invention may include physiological well tolerated excipients (see Handbook of Pharmaceutical Excipients, 5$^{th}$ ed., edited by Raymond Rowe, Paul Shesky and Sien Owen, Pharmaceutical Press (2006), such as antioxidants like ascorbic acid or glutathione, preserving agents such as phenole, m-cresole, methyl- or propylparabene, chlorobutanol, thiomersal or benzalkoiumchloride, stabilizer, framework former such as saccharose, lactose, maltose, trehalose, mannitose, mannit and/or sorbit, mannit and/or lactose and solubilizer such as polyethyleneglycols (PEG), i.e. PEG 3000, 3350, 4000, or 6000, or cyclodextrines, i.e. hydroxypropyle-β-cyclodextrine, sulfobutylethyl-β-cyclodextrine or γ-cyclodextrine, or dextranes or poploxaolmers, i.e. poloxaomer 407, poloxamer 188, or Tween 20, Twee 80. In one embodiment, pharmaceutical compositions of the present invention include one or more well tolerated excipients, selected from the group consisting of antioxidants, framework formers and stabilizers.

The peptides and polypeptides of the invention may also be delivered with an adjuvant. Adjuvants include, but are not limited to complete or incomplete Freund's adjuvant, Montanide ISA-51, Lymphocyte Activation Gene-3 (LAG-3), Toll like receptors (TLR), bacterial cell wall products, Lymphocyte Activation Gene-3 (LAG-3), Toll like receptors (TLR), bacterial cell wall products, aluminum phosphate, aluminum hydroxide, alum, and saponin. Adjuvant effects can also be obtained by injecting a variety of cytokines along with the immunogens of the invention. These cytokines include, but are not limited to IL-1, IL-2, IL-7, IL-12, and GM-CSF.

The peptides and polypeptides of the invention can also be added to professional antigen presenting cells such as dendritic cells that have been prepared ex vivo. For example, the dendritic cells could be prepared from CD34 positive stem cells from the bone marrow, or they could be prepared from CD14 positive monocytes obtained from the peripheral blood. The dendritic cells are generated ex vivo using cytokines such as GM-CSF, IL-3, IL4, TNF, and SCF. The cultured DC are then pulsed with peptides at various concentrations using standard methods that are well known in the art. The peptide-pulsed dendritic cells can then be administered intravenously, subcutaneously, or intradermally, and the immunization may also include cytokines such as IL-2 or IL-12.

The present invention is also directed to a vaccine in which an immunogen of the present invention is delivered or administered in the form of a polynucleotide encoding the a polypeptide or active fragment as disclosed herein, whereby the peptide or polypeptide or active fragment is produced in vivo. The polynucleotide may be included in a suitable expression vector and combined with a pharmaceutically acceptable carrier. For example, the peptides or polypeptides could be expressed in plasmid DNA and nonreplicative viral vectors such as vaccinia, fowlpox, Venezuelan equine encephalitis virus, adenovirus, or other RNA or DNA viruses. These examples are meant to be illustrative only and should not be viewed as self-limiting A wide variety of other vectors are available and are apparent to those skilled in the art from the description given herein. In this approach, a portion of the nucleotide sequence of the viral vector is engineered to express the peptides or polypeptides of the invention. Vaccinia vectors and methods useful in immunization protocols are described in U.S. Pat. No. 4,722,848, the disclosure of which is incorporated herein by reference in its entirety.

Regardless of the nature of the composition given, additional therapeutic agents may also accompany the immunogens of the present invention. Thus, for purposes of preventing or treating HBV infection, compositions containing the immunogens disclosed herein may, in addition, contain other anti-viral pharmaceuticals. The use of such compositions with multiple active ingredients is left to the discretion of the clinician.

In addition, the immunogens of the present invention can be used to stimulate the production of antibodies for use in passive immunotherapy, for use as diagnostic reagents, and for use as reagents in other processes such as affinity chromatography.

The present invention also relates to antibodies that react with immunogens, such as a polypeptide comprising one or more of the epitopic peptides of SEQ ID NO: 1-17 as disclosed herein. Active fragments of such antibodies are also specifically contemplated. Such antibodies, and active fragments of such antibodies, for example, and Fab structure, may react with, including where it is highly selective or specific for, an immunogenic structure comprising 2, 3, 4 or more of the epitopic peptides of the invention.

With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric (H.sub.2L.sub.2) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all antibodies have a similar overall 3 dimensional structure. This structure is often given as H.sub.2L.sub.2 and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, J. Biol. Chem. 252:6609-6616 (1777).

In all mammalian species, antibody polypeptides contain constant (i.e., highly conserved) and variable regions, and, within the latter, there are the CDRs and the so-called "framework regions" made up of amino acid sequences within the variable region of the heavy or light chain but outside the CDRs.

The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain. Such antibodies may also include fragments, such as Fab and F(ab.sub.2)' fragments, capable of reacting with and binding to any of the polypeptides disclosed herein as being receptors.

A further embodiment of the present invention relates to a method for inducing a CTL response in a subject comprising administering to subjects that express HLA A2 or B7 supertype antigens an effective (i.e., CTL-stimulating amount) of an immunogen of the invention that does not comprise the entire protein expressing the epitopic peptides disclosed herein (i.e., one that comprises less than the entire protein where the protein is a naturally occurring polypeptide) in an amount sufficient to induce a CTL response to HBV infected cells expressing at least HLA-A2 or HLA-B7, as the case may be, thereby eliciting a cellular response against said HBV infected cells.

A still further embodiment of the present invention relates to a method for inducing a CTL response in a subject, wherein the immunogen is in the form of a polynucleotide. In one non-limiting example, the method comprises administering to subjects that express HLA-A2 at least one CTL epitope, wherein said epitope or epitopes are selected from a group comprising the peptides disclosed according to the invention, and are coded within a polynucleotide sequence that does not comprise the entire protein coding region, in an amount sufficient to induce a CTL response to HBV infected cells expressing HLA-A2.

While the below examples are provided to illustrate the invention, it is to be understood that these methods and examples in no way limit the invention to the embodiments described herein and that other embodiments and uses will no doubt suggest themselves to those skilled in the art. All publications, patents, and patent applications cited herein are hereby incorporated by reference, as are the references cited therein. It is also to be understood that throughout this disclosure where the singular is used, the plural may be inferred and vice versa and use of either is not to be considered limiting. It should be borne in mind that although these examples recite specific oligopeptide sequences of the invention, as well as specific cell lines, the methodology disclosed in the examples applies equally, with any obvious modifications, to use of the other oligopeptides and cell lines disclosed herein according to the present invention.

EXAMPLE

The HLA-A2 and A24 positive liver hepatocellular carcinoma cell line HepG2 and its hepatitis B infected derivatives HepDE19 and HepG2.2.15 were cultured in Dulbecco's Modified Eagle Medium/Ham's F-12 50/50 Mix (Mediatech Inc, Manassas Va.). 293-T cells were maintained in Dulbecco's' Modified Eagle Medium and T2 cells were maintained in RPMI-1640 (Mediatech Inc). All media was supplemented with 10% fetal bovine serum (Atlanta Biologicals, Flowery Branch, Ga.), L-glutamine (300 mg/mL), 1× non-essential amino acids, 0.5 mM sodium pyruvate, and 1× penicillin/streptomycin (Mediatech Inc). Cells were maintained at 37° C. and 5% $CO_2$.

Cell lysates were prepared from HBV infected cells and MHC/peptide complexes were isolated by immunoaffinity chromatography using MHC molecule specific antibodies (Testa et al. 2012). The peptides purified from the MHC molecules were fractionated using C-18 reversed phase (RP) column (4.6 mm diameter×150 mm length) using an offline HPLC (Dionex, Sunnyvale, Calif.). The peptide containing fractions were collected and dried to 6 µL under vacuum for LC/MS/MS analysis.

Mass spectrometry experiments were carried out using LTQ (Thermo) and Orbitrap instruments interfaced with nano ultimate HPLC (Dionex). RP-HPLC purified peptide fractions were injected individually into the LC-MS/MS system to identify the sequences of the peptides. The peptides were analyzed using a Data-Dependent method. The acquired spectra data were searched against all influenza strains protein database using Proteome Discoverer (Thermo) to interpret data and derive peptide sequences.

Synthetic peptides were made and subjected to LC-MS/MS analysis under identical experimental conditions as described above and their sequences were confirmed based on their MS/MS data. Candidate peptide sequences were confirmed by comparison of their MS/MS spectra with that of their synthetic analogs.

In vitro peptide specific CTLs were generated using heparinized blood from healthy HLA-A2+ donors purchased from Research Blood Components, LLC (Brighton, Mass.). Peripheral blood mononuclear cells (PBMC) were purified using differential centrifugation following standard methods. PBMC were used to generate peptide specific CTL as described previously (Testa et al. 2012).

In vivo peptide specific CTLs were generated using HLA-A2 and HLA-A24 transgenic mice. Mice were injected with PBS alone or 10 ug of synthetic peptides in PBS or a 50:50 emulsion with Montanide ISV 51 (Seppic Inc, Fairfield, N.J.). Mice received a total of three injections, at 10 days intervals. A week after the third injection, mice were euthanized and the spleens harvested for use in T cell functional assays.

Antigen specific CTL activation was assessed by interferon-γ (IFN-γ) release as a measure using an ELISPOT assay (BD-Pharmingen, San Jose, Calif.) and a customized MILLIPLEX magnetic bead assay and CD107a (degranulation marker) expression by flow cytometry.

Seventeen epitopes including HLA-A2 and A24 specific motifs were identified (Table 1). All the peptide sequences were present in multiple genotype of HBV family. Eight HLA-A2 and A24 specific epitopes (SEQ ID: 1-8) were selected for CTL characterization. Synthetic peptides were used for CTL analysis.

TABLE 1

List of identified HBV MHC peptides, their sequences, corresponding proteins and accession ID's

| Seq ID | Peptide | Parent Protein | Accession ID |
|---|---|---|---|
| 1 | FLGGPPVCL | Surface (S) | Q0EED2 |
| 2 | ILRSFIPLL | Surface (S) | Q6WYY8 |
| 3 | FLKQQYMNL | Polymerase (P) | I0DE20 |
| 4 | FLSKQYMDL | Polymerase (P) | L7QBE1 |
| 5 | TVSTKLCKI | Polymerase (P) | Q8B4E6 |
| 6 | GGPNLDNIL | Large E | Q8QSF2 |
| 7 | LTTVPAASLLA | Large E | Q9YKJ7 |
| 8 | LTFGRETVLEN | Precore/Core (C) | Q6UFV9 |
| 9 | IYDHQHGTL | Polymerase (P) | C9ED71 |
| 10 | TVLENLVSLGV | precore/core protein [Hepatitis B virus] | gi34419971 |
| 11 | QAMQWNSLAF | large S protein [Hepatitis B virus] | gi222824657 |
| 12 | IEANKVGV | preS1 protein [Hepatitis B virus] | gi164509420 |
| 13 | AQGTLTSVPV | large S protein [Hepatitis B virus] | gi283971254 |
| 14 | VLLDCQGMLL | hepatitis surface antigen [Hepatitis B virus] | gi94466780 |
| 15 | MAARLRCQL | X protein [Hepatitis B virus] | gi260184403 |
| 16 | KVCRRIVGLLGFA | polymerase [Hepatitis B virus] | gi225675980 |
| 17 | NTNMGLKILQLLW | pre-C/C protein [Hepatitis B virus] | gi164416566 |

Identification of MHC Class I Presented Epitopes from Hepatitis B Virus Infected Cells by Nano LC/MS/MS Methods MHC class I associated peptides isolated from HBV infected cells were subjected to LC/MS/MS analysis to identify the peptides and their corresponding proteins. Employing this strategy, we identified seventeen MHC associated peptides (Seq ID: 1-17). Prior to CTL characterization experiments, we confirmed the authenticity of the peptides and selected five HLA-A2 and A24 specific peptides (Seq ID: 1-8) using their synthetic peptide analogs.

Epitopes Identified by Immunoproteomics Analysis Activate HBVspecific CTLs In Vitro To verify the presentation of these epitopes by infected cells, CTLs specific for the peptides were generated using PBMCs from healthy HLA-A2+ donors and synthetic peptides corresponding to the identified epitopes. In ELISpot assays, CTL functionality was measured by detection of antigen specific IFNγ secretion. As illustrated in FIG. 1, epitope specific CD8+ T cells were activated (as measured by IFN-gamma ELISpot) when cultured with T2s pulsed with peptides (FIG. 1A) and with HepDE19 or 293-T/A2-AdHBV cell lines (FIG. 1B). Importantly, these responses were specific as no CD8+ T cell activation was observed when the cells were cultured with normal liver, uninfected HepG2, or uninfected 293T/A2 cells (FIG. 1B)

Figure 2:
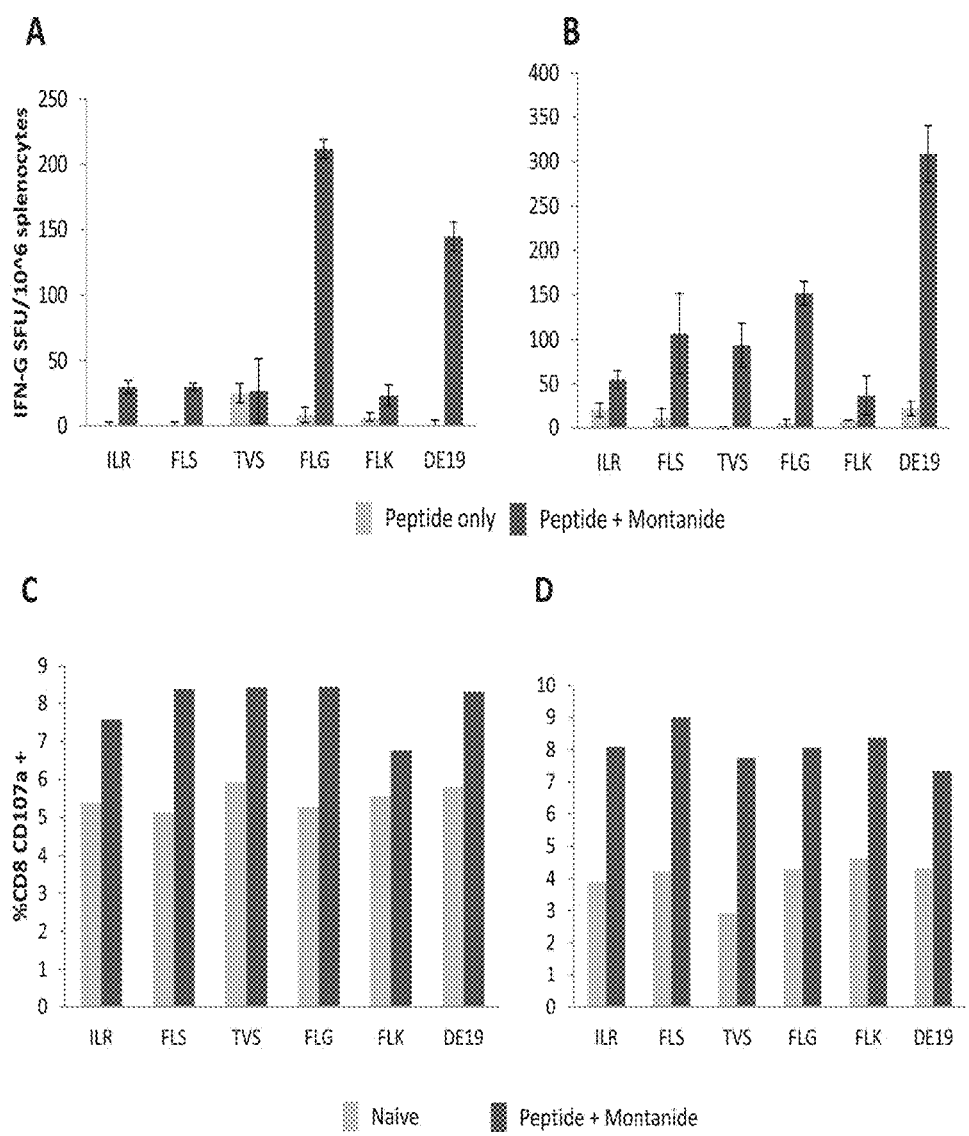
FIG. 2: HBV identified peptides are able to activate CD8+ T cells in vivo in both an HLA-A2 and HLA-A24 restricted fashion. HLA-A2 (A) or HLA-A24 (B) transgenic mice were primed and boosted with peptides as previously described. Spleens were harvested, homogenized into single cell suspensions, and cultured with peptide pulsed (peptides are represented as first 3 residues of the sequence) HepG2 cells or HBV expressing cells (DE19) overnight in an IFN-gamma ELISpot assay. T cell activation was also measured by examining CD107a upregulation on HLA-A2 (C) or HLA-A24 (D) CD8+ T cells. Splenocytes were cultured for 6 hours with peptide pulsed or HBV expressing cells in the presence of anti-CD107a and subsequently stained for CD8+ expression. Data is presented as the percent of cells in culture that are CD8+ CD107a+.

Epitopes Identified by Immunoproteomics Analysis Activate HBV specific CTLs In Vivo After establishing that epitopes could specifically induce CD8+ T cell activation in vitro, we next determined if the experimentally identified peptides could also stimulate CD8+ T cells in vivo. Because a subset of our peptides (P4-P8) had the motif to bind both HLA-A2 and HLA-A24 molecules, we assessed CD8+ T cell activation of these peptides in both contexts. Synthetic versions of peptides were injected into HLA-A2+ or HLA-A24+ transgenic mice with or without Montanide ISV-51, three times in total. One week after the third injection, splenocytes were harvested and cultured with HepG2 cells pulsed individually with peptides in an IFN-gamma ELISPot assay. As shown in FIG. 2A, CD8+ T cells generated in vivo specifically recognized peptide loaded HepG2 cells as well as HBV infected HepDE19 cells. In addition, CD8+ T cells generated in vivo also upregulated a classical marker of degranulation (CD107a) (Betts et al. 2003, Mittendorf et al. 2005) after stimulation with both peptide pulsed HepG2s and the HBV infected cell line HepDE19 (FIG. 2B). Interestingly, the peptides induced IFN-gamma secretion and CD107a upregulation independent of the HLA molecule tested which indicates that peptides are capable of binding both HLA-A2 and HLA-A24 molecules.

Figure 3:
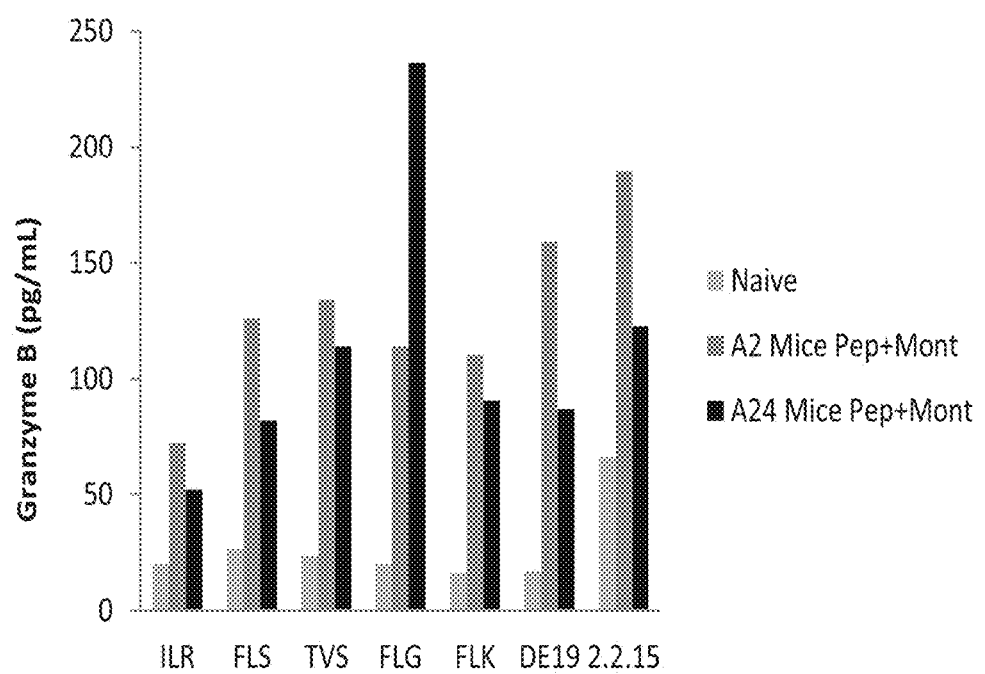
FIG. 3: CD8+ T cells activated in vivo secrete cytotoxic effector molecules. In an assay that mirrored the setup described in FIG. 2, splenocytes were cultured with peptide pulsed (peptides are represented as first 3 residues of the sequence) or HBV expressing cells (DE19 or HepG2 2.215) overnight. Supernatant was harvested and used in the Milliplex magnetic bead assay to detected granzyme B secretion in response to specific stimulation. Splenocytes from PBS primed, naïve mice were used as a negative control.

Because degranulation is associated with delivery of perform and granzyme to target cells, we next checked the levels of granzyme B being secreted by the peptide activated CD8+ T cells. Supernatants were collected from the stimulated cells and the levels of granzyme B were detected using Milliplex magnetic bead technology (Parmigiani et al. 2013; Nieminen et al. 2013). CD8+ T cells from both HLA-A2 and HLA-A24 mice secreted high levels of granzyme-B in response to peptide stimulation and HepDE19 stimulation than their naïve counterparts indicating the activation of a specific cytotoxic response (FIG. 3).

| SEQUENCE LISTING | | | |
|---|---|---|---|
| Seq ID No | Peptide | Protein | Accession ID |
| Seq ID No 1 | FLGGPPVCL | Surface (S) | Q0EED2 |
| Seq ID No 2 | ILRSFIPLL | Surface (S) | Q6WYY8 |
| Seq ID No 3 | FLKQQYMNL | Polymerase (P) | I0DE20 |
| Seq ID No 4 | FLSKQYMDL | Polymerase (P) | L7QBE1 |
| Seq ID No 5 | TVSTKLCKI | Polymerase (P) | Q8B4E6 |
| Seq ID No 6 | GGPNLDNIL | Large E | Q8QSF2 |
| Seq ID No 7 | LTTVPAASLLA | Large E | Q9YKJ7 |
| Seq ID No 8 | LTFGRETVLEN | Precore/Core (C) | Q6UFV9 |
| Seq ID No 9 | IYDHQHGTL | Polymerase (P) | C9ED71 |
| Seq ID No 10 | TVLENLVSLGV | precore/core protein [Hepatitis B virus] | gi34419971 |
| Seq ID No 11 | QAMQWNSLAF | large S protein [Hepatitis B virus] | gi222824657 |
| Seq ID No 12 | IEANKVGV | preS1 protein [Hepatitis B virus] | gi164509420 |
| Seq ID No 13 | AQGTLTSVPV | large S protein [Hepatitis B virus] | gi283971254 |
| Seq ID No 14 | VLLDCQGMLL | hepatitis surface antigen [Hepatitis B virus] | gi94466780 |
| Seq ID No 15 | MAARLRCQL | X protein [Hepatitis B virus] | gi260184403 |
| Seq ID No 16 | KVCRRIVGLLGFA | polymerase [Hepatitis B virus] | gi225675980 |
| Seq ID No 17 | NTNMGLKILQLLW | pre-C/C protein [Hepatitis B virus] | gi164416566 |

I claim:

1. A pharmaceutical composition comprising at least one peptide consisting of 8 to about 30 amino acid residues and comprising the amino acid sequence of SEQ ID NO: 2, wherein said peptide can bind to class I MHC molecules from A2 and A24 supertypes, or can be processed to bind to class I MHC molecules from A2 and A24 supertypes, and activate a T lymphocyte response and wherein the peptide is in the form of a pharmaceutically acceptable salt.

2. The pharmaceutical composition of claim 1 wherein said peptide comprises at least two epitopic peptides.

3. The pharmaceutical composition of claim 1 wherein said peptide comprises at least three epitopic peptides.

4. The pharmaceutical composition of claim 1 wherein said peptide comprises at least four epitopic peptides.

5. The pharmaceutical composition of claim 1 wherein said peptide differs from SEQ ID NO: 2 by no more than one amino acid unit, and wherein said one amino acid difference is the result of a conservative amino acid substitution.

6. The pharmaceutical composition of claim 5 wherein said conservative amino acid substitution is the substitution of one hydrophobic amino acid with another hydrophobic amino acid.

7. A method for vaccinating and treating a subject for HBV infection, said subject comprising infected cells expressing any class I MHC molecule, comprising administering to said subject a pharmaceutical composition in an amount sufficient to induce a CTL response to said infected cells, wherein said pharmaceutical composition comprises:

a. at least one peptide consisting of 8 to about 30 amino acid residues and comprising the amino acid sequence of SEQ ID NO: 2; or b. at least one peptide consisting of 8 to about 30 amino acid residues and comprising an amino acid sequence that differs from SEQ ID NO 2 by no more than one amino acid, wherein said one amino acid difference is the result of a conservative amino acid substitution wherein said peptide can bind to class 1 MHC; molecules from A2 and A24 supertypes, or can be processed to bind to class 1 MHC molecules from A2 and A24 supertypes, and activate a T lymphocyte response and wherein the peptide is in the form of a pharmaceutically acceptable salt.

8. A method for vaccinating humans against HBV infection using a pharmaceutical composition comprising:

a. at least one peptide consisting of 8 to about 30 amino acid residues and comprising the amino acid sequence of SEQ ID NO: 2; or b. at least one peptide consisting of 8 to about 30 amino acid residues and comprising an amino acid sequence that differs from SEQ ID NO: 2 by no more than one amino acid, wherein said one amino acid difference is the result of a conservative amino acid substitution;

wherein said peptide can bind to class 1 MHC molecules from A2 and A24 supertypes, or can be processed to bind to class 1 MHC molecules from A2 and A24 supertypes, and activate a T lymphocyte response and wherein the peptide is in the form of a pharmaceutically acceptable salt.

* * * * *

SEQUENCE LISTING

<160> NUMBER OF SEQ ID NOS: 17

<210> SEQ ID NO 1
<211> LENGTH: 9
<212> TYPE: PRT
<213> ORGANISM: Hepatitis B virus

<400> SEQUENCE: 1

Phe Leu Gly Gly Pro Pro Val Cys Leu
1               5

<210> SEQ ID NO 2
<211> LENGTH: 9
<212> TYPE: PRT
<213> ORGANISM: Hepatitis B virus

<400> SEQUENCE: 2

Ile Leu Arg Ser Phe Ile Pro Leu Leu
1               5

<210> SEQ ID NO 3
<211> LENGTH: 9
<212> TYPE: PRT
<213> ORGANISM: Hepatitis B virus

<400> SEQUENCE: 3

Phe Leu Lys Gln Gln Tyr Met Asn Leu
1               5

<210> SEQ ID NO 4
<211> LENGTH: 9
<212> TYPE: PRT
<213> ORGANISM: Hepatitis B virus

<400> SEQUENCE: 4

Phe Leu Ser Lys Gln Tyr Met Asp Leu
1               5

<210> SEQ ID NO 5
<211> LENGTH: 9
<212> TYPE: PRT
<213> ORGANISM: Hepatitis B virus

<400> SEQUENCE: 5

Thr Val Ser Thr Lys Leu Cys Lys Ile
1               5

<210> SEQ ID NO 6
<211> LENGTH: 9
<212> TYPE: PRT
<213> ORGANISM: Hepatitis B virus

<400> SEQUENCE: 6

Gly Gly Pro Asn Leu Asp Asn Ile Leu
1               5

<210> SEQ ID NO 7
<211> LENGTH: 11
<212> TYPE: PRT
<213> ORGANISM: Hepatitis B virus

<400> SEQUENCE: 7

Leu Thr Thr Val Pro Ala Ala Ser Leu Leu Ala
1               5                   10

```
<210> SEQ ID NO 8
<211> LENGTH: 11
<212> TYPE: PRT
<213> ORGANISM: Hepatitis B virus

<400> SEQUENCE: 8

Leu Thr Phe Gly Arg Glu Thr Val Leu Glu Asn
1               5                   10

<210> SEQ ID NO 9
<211> LENGTH: 9
<212> TYPE: PRT
<213> ORGANISM: Hepatitis B virus

<400> SEQUENCE: 9

Ile Tyr Asp His Gln His Gly Thr Leu
1               5

<210> SEQ ID NO 10
<211> LENGTH: 11
<212> TYPE: PRT
<213> ORGANISM: Hepatitis B virus

<400> SEQUENCE: 10

Thr Val Leu Glu Asn Leu Val Ser Leu Gly Val
1               5                   10

<210> SEQ ID NO 11
<211> LENGTH: 10
<212> TYPE: PRT
<213> ORGANISM: Hepatitis B virus

<400> SEQUENCE: 11

Gln Ala Met Gln Trp Asn Ser Leu Ala Phe
1               5                   10

<210> SEQ ID NO 12
<211> LENGTH: 8
<212> TYPE: PRT
<213> ORGANISM: Hepatitis B virus

<400> SEQUENCE: 12

Ile Glu Ala Asn Lys Val Gly Val
1               5

<210> SEQ ID NO 13
<211> LENGTH: 10
<212> TYPE: PRT
<213> ORGANISM: Hepatitis B virus

<400> SEQUENCE: 13

Ala Gln Gly Thr Leu Thr Ser Val Pro Val
1               5                   10

<210> SEQ ID NO 14
<211> LENGTH: 10
<212> TYPE: PRT
<213> ORGANISM: Hepatitis B virus

<400> SEQUENCE: 14

Val Leu Leu Asp Cys Gln Gly Met Leu Leu
1               5                   10

<210> SEQ ID NO 15
```

```
<211> LENGTH: 9
<212> TYPE: PRT
<213> ORGANISM: Hepatitis B virus

<400> SEQUENCE: 15

Met Ala Ala Arg Leu Arg Cys Gln Leu
1               5

<210> SEQ ID NO 16
<211> LENGTH: 13
<212> TYPE: PRT
<213> ORGANISM: Hepatitis B virus

<400> SEQUENCE: 16

Lys Val Cys Arg Arg Ile Val Gly Leu Leu Gly Phe Ala
1               5                   10

<210> SEQ ID NO 17
<211> LENGTH: 13
<212> TYPE: PRT
<213> ORGANISM: Hepatitis B virus

<400> SEQUENCE: 17

Asn Thr Asn Met Gly Leu Lys Ile Leu Gln Leu Leu Trp
1               5                   10
```